US006428821B2

(12) United States Patent
Woo et al.

(10) Patent No.: US 6,428,821 B2
(45) Date of Patent: Aug. 6, 2002

(54) ORAL MICRO-EMULSION COMPOSITION OF SILYBIN

(76) Inventors: Jong-Soo Woo, Cheoncheonjugong Apt. 118-203, #333, Cheoncheon-dong, Jang-gu, Kyungki-do (KR), 440-330; Heun-Joo Suh, LG Village 411-903, #520, Kumkog-dong, Kwonsungu, Kyungki-do (KR), 441-460

( * ) Notice: Subject to any disclaimer, the term of this patent is extended or adjusted under 35 U.S.C. 154(b) by 0 days.

(21) Appl. No.: 09/775,704

(22) Filed: Feb. 2, 2001

Related U.S. Application Data

(63) Continuation of application No. PCT/KR00/00720, filed on Jul. 5, 2000, now abandoned.

(30) Foreign Application Priority Data

Jul. 5, 1999 (KR) .............................. 99-26809

(51) Int. Cl.⁷ ........................ A61K 35/78; A01N 37/18
(52) U.S. Cl. ........................ 424/764; 424/776; 514/893; 514/937; 514/2
(58) Field of Search ................................ 424/764, 725, 424/776; 514/2, 78, 452, 893, 937

(56) References Cited

U.S. PATENT DOCUMENTS 4,061,765 A * 12/1977 Madaus et al.
4,895,839 A * 1/1990 Bombardelli

* cited by examiner

*Primary Examiner*—Christopher R. Tate
*Assistant Examiner*—Michele C. Flood
(74) *Attorney, Agent, or Firm*—Katten Muchin Zavis Rosenman

(57) ABSTRACT

An oral micro-emulsion composition comprising a *Carduus marianus* extract, silybin or a silybin derivative; an organic solvent; a surfactant; and an oil provides a high in vivo bioavailability of silybin.

5 Claims, 1 Drawing Sheet

● : EXAMPLE 1
▲ : LEGARON®140 CAPSULE
■ : LEGARON®TABLET

ORAL MICRO-EMULSION COMPOSITION OF SILYBIN

CROSS REFERENCE TO RELATED APPLICATION

This application is a continuation of International Application PCT/KR00/00720, with an international filing date of Jul. 5, 2000, now abandoned.

FIELD OF THE INVENTION

The present invention relates to an oral silybin composition having improved silybin bioavailability and more particularly, to a micro-emulsion composition comprising a *Carduus marianus* extract or silybin.

BACKGROUND OF THE INVENTION

Silybin, the primary component of a *Carduus marianus* extract, is known to have excellent activity in protecting liver cells from harmful effects caused by smoking, drinking, overworking, environmental contaminants, stress or liver-damaging drugs. However, the bioavailability of orally administered silybin is very low due to its low solubility in water.

Korean Patent Publication No. 96-13361 teaches a method for increasing the solubility of silybin by dissolving silybin in a mixture of polyethylene glycol and ethanol, and adding the resulting solution to an aqueous polysorbate solution to formulate a silybin solution. However, this method has the problem that the incremental increase in the silybin solubility is only marginal, requiring the use of a large amount of the aqueous solution.

Korean Patent Publication No. 96-777 discloses a silybin complex preparation using a mono- or disaccharide, a cellulose derivative or 1-vinyl-2-pyrrolidone as an excipient and having 2-fold higher silybin bioavailability as compared with conventional formulations. This preparation is commercially available from Bugwang Medicine under the trade name of Legaron® 140 capsule. However, the manufacturing process of the above preparation is very complicated and the in vivo bioavailability of silybin achievable is still limited.

Accordingly, there has existed a need to develop an oral silybin composition having improved in vivo bioavailability of silybin.

SUMMARY OF THE INVENTION

It is, therefore, an object of the present invention to provide an improved oral composition of silybin.

In accordance with one aspect of the present invention, there is provided a micro-emulsion composition for oral administration comprising a *Carduus marianus* extract, silybin or a silybin derivative; an organic solvent as co-surfactant; a surfactant; and an oil.

BRIEF DESCRIPTION OF THE DRAWINGS

The above and other objects and features of the present invention will become apparent from the following description of the invention, when taken in conjunction with the accompanying drawing, FIG. 1, which shows the bioavailabilities of the inventive silybin preparation and commercially available silybin preparations.

DETAILED DESCRIPTION OF THE INVENTION

Figure 1:
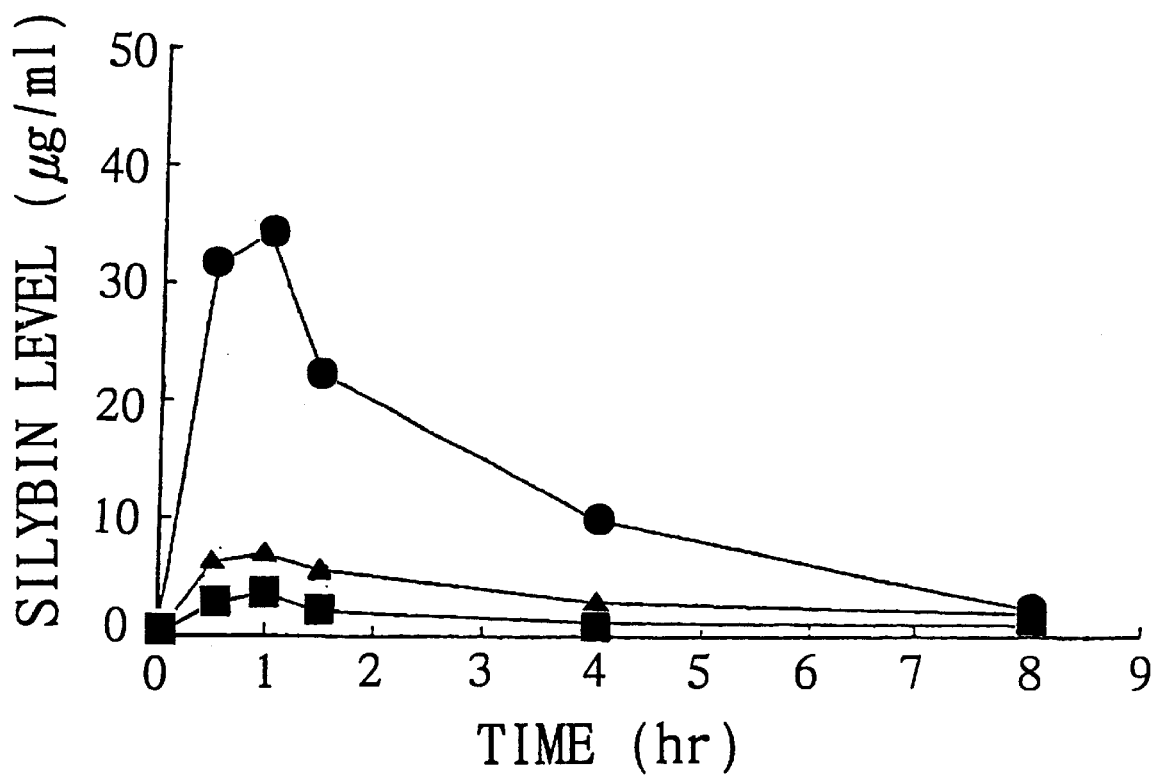

The inventive oral composition, which comprises a *Carduus marianus* extract containing a major amount of silybin, silybin or a silybin derivative as an active ingredient in a stable emulsion form, provides a greatly increased level of in vivo bioavailability of silybin, the level being at least 4-fold higher than that achievable by conventional formulations. Representative examples of the silybin derivative include silycristin, silydiamin and isosilybin. A commercially available *Carduus marianus* extract typically contains silybin in an amount of about 30% or more.

The inventive composition comprising a *Carduus marianus* extract, silybin or a silybin derivative contains as a co-surfactant an organic solvent which is both hydrophilic and hydrophobic. The co-surfactant assists the formulation of a uniform emulsion of the active ingredient and keeps the emulsion stable during a storage. The co-surfactant which may be used in the present invention is ethanol, propylene glycol(1,2-dihydroxypropane), polyethylene glycol, e.g., having a molecular weight of 200 to 600, propylene carbonate(4-methyl-2-oxo-1,3-dioxolane), transcutol (diethyleneglycol monoethyl ether), glycofurol (tetrahydrofurfuryl alcohol polyethylene glycol ether), dimethyl isosorbide(1,4:3,6-dianhydro-2,5-dimethyl-D-glucitol) or a mixture thereof, wherein dimethyl isosorbide is preferred.

The oral composition of the present invention further comprises a surfactant which promotes the wetting of the active ingredient in an aqueous medium. Representative examples of the surfactant include:

(1) polyoxyethylene glycolated natural or hydrogenated vegetable oils such as polyoxyethylene glycolated natural or hydrogenated castor oil(Cremophor® and HCO®, BASF), (2) polyoxyethylene-sorbitan-fatty acid esters wherein fatty acid is mono- or tri-lauric, palmitic, stearic or oleic acid (Tween®, ICI), (3) polyoxyethylene fatty acid esters such as polyoxyethylene stearic acid ester (Myrj®, ICI), (4) polyoxyethylene-polyoxypropylene copolymer (Pluronic®, BASF), (5) polyoxyethylene-polyoxypropylene block copolymer (Poloxamer®, BASF), (6) sodium dioctyl sulfosuccinate or sodium lauryl sulfate, (7) phospholipids, (8) propylene glycol mono- or di-fatty acid esters such as propylene glycol dicaprylate, propylene glycol dilaurate, propylene glycol isostearate, propylene glycol laurate, propylene glycol ricinoleate and propylene glycol caprylic-capric acid diester (Miglyol® 840, H ls), (9) trans-esterification products of natural vegetable oil triglycerides and polyalkylene polyols (Labrafil® M, Gattefosse),

(10) mono-, di- or mono/di-glycerides such as caprylic/capric acid mono- and di-glycerides (Imwitor®, H ls),

(11) sorbitan fatty acid esters such as sorbitan monolauryl, sorbitan monopalmityl and sorbitan monostearyl esters (Span®, ICI), and

(12) sterols or derivatives thereof such as cholesterol, pytosterol and cytosterol.

Among the above-mentioned surfactants, polyoxyethylene glycolated natural or hydrogenated vegetable oils and polyoxyethylene-sorbitan-fatty acid esters are preferably used in the present invention.

The oral composition of the present invention still further comprises an oil which is compatible with the co-surfactant and surfactant components to form a stable emulsion. Representative examples of the oil include:

(1) fatty acid triglycerides, preferably medium fatty acid triglycerides, such as fractionated coconut oil (Miglyol® 812N, H 1s),
(2) mono-, di- or mono/di-glycerides, preferably mono- or di-glycerides of oleic acid,
(3) esters of fatty acids and monovalent alkanols, preferably esters of $C_{8-20}$ fatty acids and $C_{2-3}$ monovalent alkanols, such as isopropyl myristate, isopropyl palmitate, ethyl linoleate and ethyl oleate,
(4) natural vegetable or animal oils such as corn oil, olive oil, soybean oil and fish oil,
(5) carbohydrates such as squalene and squalane, and
(6) free fatty acids such as oleic acid and linoleic acid in a fluid form.

Among above-mentioned oil, medium fatty acid triglycerides, mono-, di- or mono/di-glycerides and esters of fatty acids and monovalent alkanols are preferably employed in the present invention.

In accordance with the present invention, the silybin or silybin derivative:co-surfactant:surfactant:oil weight ratio is in the range of 1:1~20:1~20:0.5~20, preferably, 1:5~15:5~15:1~10.

In addition, the inventive composition may comprise pharmaceutically acceptable additives for an oral administration, e.g., viscosity controlling agents, aromatics, anti-oxidants and preservatives.

The inventive composition may be prepared by mixing and dissolving said components uniformly, and form a micro-emulsion of below 1 μm on contacting an aqueous solution.

The pharmaceutical composition of the present invention may be formulated into various pharmaceutical preparations, e.g., powder, granule, tablet, coated preparation and liquid preparation, in accordance with any of the conventional procedures. For instance, a hard capsule may be prepared by adding a lubricant and other pharmaceutical additives to the pharmaceutical composition, processing the mixture into a powder or granules and filling the powder or granules into a hard gelatin capsule; a tablet, by adding a suitable additive to the pharmaceutical composition and tableting the mixture; a liquid preparation, by dissolving the pharmaceutical composition in water; and a coated preparation, by coating a solution of the pharmaceutical composition on a sugar bead such as Non-pareil® (Edward Mendell Co., UK). In case of adults, a typical daily dose of silybin may range from about 45 to 180 mg and can be administered in a single dose or in divided doses.

As described above, the inventive composition gives a remarkably high in vivo bioavailability of silybin.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Preparation of Soft Capsule

A soft capsule was prepared using the following ingredients:

|  | Quantity (mg/capsule) |
| --- | --- |
| *Carduus marianus* extract (as silybin) | 100 |
|  | (30) |
| Dimethyl isosorbide | 265 |
| HCO ® 50 | 160 |
| Tween ® 20 | 160 |
| Miglyol ® 812N | 24 |
| Ethyl linoleate | 90 |
| Glyceril mono-oleate | 40 |
| D-α-tocopherol as an anti-oxidant | 6 |

The *Carduus marianus* extract and dimethyl isosorbide were mixed and dissolved uniformly, and other ingredients were added thereto and dissolved. Then, the resulting mixture was filled into a soft capsule which was prepared using succinic acid, gelatin, glycerin and purified water by a conventional method.

EXAMPLE 2

Preparation of Soft Capsule

A soft capsule was prepared by the procedure of Example 1 using the following ingredients:

|  | Quantity (mg/capsule) |
| --- | --- |
| *Carduus marianus* extract (as silybin) | 50 |
|  | (15) |
| Dimethyl isosorbide | 133 |
| HCO ® 50 | 80 |
| Tween ® 20 | 80 |
| Miglyol ® 812N | 12 |
| Ethyl linoleate | 45 |
| Glyceril mono-oleate | 20 |
| D-α-tocopherol as an anti-oxidant | 3 |

EXAMPLE 3

Preparation of Soft Capsule

A soft capsule was prepared by the procedure of Example 1 using the following ingredients:

|  | Quantity (mg/capsule) |
| --- | --- |
| *Carduus marianus* extract (as silybin) | 50 |
|  | (15) |
| Dimethyl isosorbide | 133 |
| Cremophor ® RH40 | 100 |
| Tween ® 20 | 80 |
| Miglyol ® 812N | 12 |

-continued

| | Quantity (mg/capsule) |
|---|---|
| Glyceril mono-oleate | 40 |
| D-α-tocopherol as an anti-oxidant | 3 |

EXAMPLE 4

Preparation of Soft Capsule

A soft capsule was prepared by the procedure of Example 1 using the following ingredients:

| | Quantity (mg/capsule) |
|---|---|
| *Carduus marianus* extract (as silybin) | 50 (15) |
| Polyethylene glycol 200 | 160 |
| HCO ® 50 | 80 |
| Tween ® 20 | 100 |
| Miglyol ® 812N | 30 |
| Ethyl linoleate | 30 |
| Glyceril mono-oleate | 30 |
| D-α-tocopherol as an anti-oxidant | 2 |

EXAMPLE 5

Preparation of Soft Capsule

A soft capsule was prepared by the procedure of Example 1 using the following ingredients:

| | Quantity (mg/capsule) |
|---|---|
| *Carduus marianus* extract (as silybin) | 100 (30) |
| Dimethyl isosorbide | 265 |
| HCO ® 50 | 160 |
| Poloxamer ® | 130 |
| Miglyol ® 812N | 40 |
| Oleic acid | 20 |
| Glyceril mono-oleate | 40 |
| D-α-tocopherol as an anti-oxidant | 6 |

TEST EXAMPLE 1

In Vivo Absorption Test

In order to investigate the bioavailability of silybin contained in the inventive preparations, in vivo absorption tests were conducted out for the inventive preparation of Example 1, Legaron® tablet (Bugwang Medicine) and Legaron® 140 capsule (Bugwang Medicine), as follows.

Fifteen 14- to 15-week-old male Sprague-Dawly rats each weighing about 300 g were fasted for over 48 hours while they were allowed free access to water, and then divided into three groups each containing 5 rats.

The three groups of rats were orally administered with the inventive preparation of Example 1, Legaron® tablet and Legaron® 140 capsule, respectively, in a dose of 60 mg silybin/kg body weight of the rat. Blood samples were taken directly from the hearts of the rats before and 0.5, 1, 1.5, 4 and 8 hours after the administration, and sera were separated therefrom.

Added to 500 µl each of the serum samples were 50 µl of an internal standard solution (methanol solution containing 2.0 µg/ml of naringenin), 900 µl of 0.5 M sodium acetate solution (pH 5.0) and 100 µl of an enzyme solution (0.5 M sodium acetate solution (pH 5.0) of β-glucuronidase 13.48 units/sulphatase 4.5 units), and after mixing for 5 min., the mixture was kept at 37° C. for 4 hours. 1.5 ml of 1 M sodium carbonate (pH 8.5) was added thereto and the mixture was shaken for 10 min., and then 5 ml of ether was added thereto and the resulting mixture was shaken for 15 min. to obtain an extract. The extract was centrifuged at 2,000 rpm for 10 min. and 4.2 ml of the solvent was evaporated at 30° C. under a nitrogen atmosphere. To the resulting residue was added 250 µl of a mixture of methanol and 10 mM sodium dihydrogen phosphate (50:50) and the mixture was subjected to HPLC under the following conditions. The observed results are shown in Table 1 and FIG. 1:

column: Inertsil ODS2 (250×4.6 mm, 5 µm; GL science, Japan)

mobile phase: methanol: 10 mM sodium dihydrogen phosphate=50:50 (pH 3.0 by phosphoric acid)

detector: UV 285 nm flow rate: 1.0 ml/min.

injection volume: 50 µl

TABLE 1

| | Total amounts of silybin (µg/ml) | | | | | |
|---|---|---|---|---|---|---|
| | 0 hr | 0.5 hr | 1 hr | 1.5 hrs | 4 hrs | 8 hrs |
| Example 1 | 0 | 31.7 | 34.3 | 22.3 | 9.7 | 2.3 |
| Legaron ® tablet | 0 | 2.7 | 3.7 | 2.1 | 1.2 | 0.9 |
| Legaron ® 140 capsule | 0 | 6.1 | 7.0 | 5.5 | 2.8 | 1.8 |

The results in Table 1 and FIG. 1 shows that the bioavailability of silybin observed for the inventive preparation is much higher as compared to Legaron® tablet and Legaron® 140 capsule.

While the invention has been described with respect to the above specific embodiments, it should be recognized that various modifications and changes may be made to the invention by those skilled in the art which also fall within the scope of the invention as defined by the appended claims.

What is claimed is:

1. A micro-emulsion composition for oral administration comprising a *Carduus marianus* extract; an organic co-surfactant; a surfactant; and an oil, said *Carduus marianus* extract comprising silybin or a silybin derivative; and being prepared by pressing and grinding the seeds of *Carduus marianus*, and extracting the resultant product with an organic solvent; and, wherein the silybin or silybin derivative:co-surfactant:surfactant:oil ratio by weight is in the range of 1:1~20:1~20:0.5~20.

2. The micro-emulsion composition of claim 1, wherein the silybin derivative is silycristin, silydianin or isosilybin.

3. The micro-emulsion composition of claim 1, wherein the co-surfactant is selected from the group consisting of: ethanol, propylene glycol, polyethylene glycol, propylene carbonate, transcutol, glycofurol, dimethyl isosorbide and a mixture thereof.

4. The micro-emulsion composition of claim 1, wherein the surfactant is selected from the group consisting of:

polyoxyethylene glycolated natural or hydrogenated vegetable oils, polyoxyethylene-sorbitan-fatty acid esters, polyoxyethylene fatty acid esters, polyoxyethylene-polyoxypropylene copolymer, polyoxyethylene-polyoxypropylene block copolymer, sodium dioctyl sulfosuccinate, sodium lauryl sulfate, phospholipids, propylene glycol mono- or di-fatty acid esters, trans-esterification products of natural vegetable oil triglycerides and polyalkylene polyols, monoglycerides, diglycerides, mono/di-glycerides, sorbitan fatty acid esters, sterols or derivatives thereof and a mixture thereof.

5. The micro-emulsion composition of claim 1, wherein the oil is selected from the group consisting of: fatty acid triglycerides, mono-, di- or mono/di-glycerides, esters of fatty acids and monovalent alkanols, natural vegetable or animal oils, squalene, squalane, oleic acid, linoleic acid and a mixture thereof.

* * * * *